| United States Patent [19] | [11] Patent Number: 4,713,348 |
| Ullman | [45] Date of Patent: * Dec. 15, 1987 |

[54] FLUORESCENT MULTIPARAMETER PARTICLE ANALYSIS

[75] Inventor: Edwin F. Ullman, Atherton, Calif.

[73] Assignee: Syntex (U.S.A.) Inc., Palo Alto, Calif.

[*] Notice: The portion of the term of this patent subsequent to Apr. 22, 2003 has been disclaimed.

[21] Appl. No.: 790,291

[22] Filed: Oct. 22, 1985

Related U.S. Application Data

[63] Continuation of Ser. No. 482,124, Apr. 5, 1983, Pat. No. 4,584,277.

[51] Int. Cl.$^4$ ................ G01N 33/566; G01N 33/554; G01N 33/544
[52] U.S. Cl. .................................. 436/501; 436/172; 436/518; 436/519; 436/520; 436/521; 436/528; 436/529; 436/530; 436/531; 436/800; 436/805; 436/808; 424/11
[58] Field of Search .................. 436/501, 518–521, 436/523, 528–531, 800, 805, 808, 172; 424/11

[56] References Cited

U.S. PATENT DOCUMENTS 4,499,052 2/1985 Fulwyler ........................... 436/172
4,511,662 4/1985 Baran et al. ....................... 436/531

OTHER PUBLICATIONS

Mirro, Jr. et al., J. Immunol. Methods, 47(1981)39–48.

*Primary Examiner*—Christine M. Nucker
*Attorney, Agent, or Firm*—Theodore Leitereg; Bertram Rowland

[57] ABSTRACT

Methods are provided for rapidly determining a number of parameters in a few determinations. Particularly, the method is applicable to blood typing, determining the blood type as to the ABO and Rh type, as well as the determination of isoantibodies to the antigens. The method employs fluorescent particles having a plurality of fluorescers, where the presence or absence of light emission of a particular wavelength can be determined.

14 Claims, No Drawings

FLUORESCENT MULTIPARAMETER PARTICLE ANALYSIS

This is a continuation of application U.S. Ser. No. 482,124, filed on Apr. 5, 1983, and U.S. Pat. No. 4,584,277.

BACKGROUND OF THE INVENTION

1. Field of the Invention

The continued dependence upon whole blood obtained from individuals for replenishing blood in another person requires the monitoring of large volumes of blood for their blood group type. In determining the blood group, one is interested in a number of factors: The particular type in the ABO group; the presence of isoantibodies to the antigens of the ABO group; and the Rh type. Where each of these factors must be determined independently, a large number of tests are involved. For the most part, hemagglutination tests have been involved in measuring the various factors, which are subjective labor intensive and cumbersome. Furthermore, they have not readily lent themselves to automation, so that the tests can be run rapidly with minimum involvement of a technician. It is therefore desirable to find techniques which allow for minimal numbers of determination, automation of the method of determination, while accurately reporting the information necessary for blood typing.

2. Brief Description of the Prior Art

Hoffman et al., *Int. J. Immunopharmac.* (1981) 3(3): 249–254 describes immunofluorescent analysis of blood cells by flow cytometry. Methods for measuring fluorescent beads may be found in Briggs et al., *Science* (1981) 212: 1266–1267 and Nicoli et al., *PNAS USA* (1980) 77: 4904–4908. See also copending application Ser. No. 397,285, filed July 12, 1982, which disclosures incorporate herein by reference, as describing an alternate technique for measuring fluorescent cells. For a general discription, see Flow Cytometry and Sorting, (eds. Melamed et al.) John Wiley and Sons, New York, 1979.

SUMMARY OF THE INVENTION

Methods and compositions are provided for assaying in bulk solution a multiparameter sample in a minimum number of determinations without employing restricted flow or separations. The method employs particles and fluorescent labels, where light signals are simultaneously or sequentially determined as indicative of a component in the assay medium. Illustrative of the technique is the typing of a single suspension of a whole blood sample as to ABO group and isoantibodies, and the determination of the special A,B, isoantibodies and Rh factor. The former determination employs A and B phenotype particles distinguishable from native erythrocytes. Fluorescent antibodies are employed where independently determined fluorescent measurements can be related to the parameter of interest.

DESCRIPTION OF THE SPECIFIC EMBODIMENTS

In accordance with the subject invention, novel methods and compositions are provided for determining a plurality of parameters in a sample with a minimum number of determinations. The method involves the use of particles and one or more fluorescers and the detection of at least two distinguishable signals. Depending on the number of signals determined based on the same or different valued spectroscopic characteristics, with a single determination, two signals can distinguish two parameters. With an increasing number of signals, greater numbers of parameters may be determined. In general, with n signals one can distinguish $2^{n-1}$ parameters. Usually not more than three signals will be employed, allowing for a determination of 4 parameters.

The determinations involve inspecting a single particle as to whether an observed signal differs from a threshold value by a predetermined amount positive or negative. Depending on the parameters of interest, there will be populations of particles with signals above or below a predetermined threshold, which will define the presence or absence of the particular parameter. The parameters are epitopic sites and binding sites of specific binding members which are ligands and receptors, respectively.

In many situations there is an interest in determining the presence, absence or coexistence of a plurality of parameters. For example, in HLA typing, one can be interested in determining the presence or absence of particular combinations of subtypes. Another area of interest can be the determination of the presence of cell surface proteins. There is also the area of blood typing involving antigenic sites on cell surfaces and antibodies to phenotypes. Of course, this invention need not be restricted to cells, since there will be other situations where one is concerned with the simultaneous presence of two parameters, which may be physically associated or dissociated.

In performing the subject invention one uses a single suspension where dye reagents, particularly fluorescent reagents, either the same or different, may be added concomitantly or sequentially. One then distinquishes between individual reagent molecules dispersed in solution and groups of reagent molecules in relatively close proximity. The assembling or grouping of the dye molecules on a particle provides for a substantial difference in signal due to the substantially higher concentration of dye reagent associated with an individual particle which is being monitored. By monitoring a sufficiently small volume, so that on the average only one particle is being inspected at a time, and making a large number of measurements of such sized volume, which monitored volumes differ temporally or spatially, one determines the proportion of particles (i.e. volumes) associated with a signal differing from a predetermined threshold value. Based on the number of volumes providing signal(s) exceeding a predetermined value, one can identify the presence or absence of a plurality of parameters.

The sample will be continuous, being still or stirred and not a moving stream. That is, one monitors a portion of a sample which remains in a diffusive relationship with the entire sample being measured.

The reagents which are employed will be dye, particularly fluorescer labeled specific binding members and particles or unlabeled particles, so long as the particle reagent is distinguishable from particles present in the sample medium. The reagents may be the same as the binding member having the parameter or analogous to such binding member by having the same or substantially the same binding properties. For example, where the parameter is an antibody binding site, the reagent could be on Fab fragment, F(ab')$_2$, etc. Where the parameter is the determinant site of a ligand, one could employ an oligopeptide having analogous binding properties, which can compete with the parameter epitopic site for a reciprocal receptor.

A wide variety of protocols may be employed depending upon the number of parameters of interest and the choice of reagents. For example, for the measurement X and anti-Y where X is bound to a particle, one can determine X with only fluorescer labeled anti-X (F-anti-X) and anti-Y with a Y-labeled particle and fluorescer labeled anti-Y (F-anti-Y), where the Y-labeled particle can be distinquished from the X-bound particle.

The protocol would be adding F-anti-X to the sample and determining whether the F-anti X becomes bound to X-bound sample particles. One then adds the Y-labeled particles and F-anti-Y and determines if the number of fluorescent labeled particles has increased to a level indicative of the absence of anti Y. In this manner two sequential measurements are made with the same sample and in the same apparatus. Employing a carousel, the additions and determinations can be automated.

There is the opportunity to use a single fluorescer, where sequential additions and sequential measurements are made. For example, consider the measurement of a sample of particles which may or may not have X and/or Y. One could first add F-anti-X and measure the number of particles which fluoresce above a predetermined threshold value. One would then add F-anti-Y (the two Fs are the same fluorescer) and determine the number of particles having a predetermined value greater than the value observed after the addition of F-anti-X. By having sequential additions and measurements, the necessity for measuring light at two different wavelengths can be obviated.

A particular application for the subject method is in blood typing where various combinations of parameters are of interest. The following Table 1 indicates various parameters of interest, the number of fluorophores required and the nature of the reagents.

TABLE 1

| Analytes | No. of Fluorophores | Reagents |
|---|---|---|
| A; B; αA; αB | 2 | $M_B^4$; αA-$F_1$; αB-$F_2$ |
| A; αA | 1 | M-A; αA-$F_1$ |
| B; αB | 1 | M-B; αB-$F_1$ |
| A; B | 2 | αA-$F_1$; αB-$F_2$ |
| αA; αB (plasma) | 1 | E-A; αA-$F_1$; M-B; αB-$F_1$ |
| αA; αB | 2 | $M_B^4$; α-$F_1$; αB-$F_2$ |
| αA; αB | 2 | M-A; M-B; αA-$F_1$; αB-$F_2$ |
| A; Rh | 2 | αA-$F_1$; αRh-$F_2$ |
| A; B; Rh | 3 | αA-F ; αB-$F_2$; αRh-$F_3$ |
| A; B; (A,B) | 3 | α(A,B)-$F_1$; αA-$F_2$; αB-$F_3$ |
| (A,B); Rh | 2 | α(A,B)-$F_1$; αRh-$F_2$ |
| A; B; αA; αB | 2 | M-A; M-B; αA-$F_1$; αB-$F_2$ |

All assays can be run with whole blood except where indicated. When only antigens are determined the assay may be run with isolated cells. When only antibodies are determined the assay may be run with serum or plasma. M means particle distinct from an erythrocyte (E); e.g. ghost, vesicle, or latex that is detectiblely light or by means of an additional fluorophore. αX means antiX antibodies. The combination assays may provide for determination of 2 to 4 parameters in a single assay medium, a single assay medium providing 4 parameters being the most efficient.

In blood typing one will normally be interested in obtaining the maximum amount of information from a single determination. In accordance with the protocols of this invention one can determine a variety of parameters of interest to blood typing. By having two independent determinations, one can determine the ABO type, the presence or absence of isoantibodies to the A and B antigens, the Rh type and the special A, B type. (The special A, B type involves a small percentage of the population where the A antigen binds only weakly to the usual antiserum for detecting the A antigen.) The method requires the use of from two to three labels which can be independently distinquished. Conveniently, these labels are fluorescers, which have emission characteristics which are readily distinguishable. The method involves independently, conveniently simultaneously, determining the presence or absence of the different labels on an individual particle and distinguishing native erythrocytes from A and B or AB phenotype particles.

The measurement is based on having three parameters, of which at least two are fluorescers having different emission maxima, so that they can be distinquished, while being capable of being excited by from 1 to 2 light sources. A third parameter is involved which is associated with a particle having the A and/or B antigens. The third parameter will afford a detectable distinction between the erythrocytes present in the blood sample and the particle which serves as a reagent and has the A and/or B antigens. This reagent will be referred to as M, and M refers to a marked particle, which marker or distinction from an erythrocyte may be inherent in the nature of the particle or may be as a result of a fluorescer label bound to the particle. The distinction provides a detectable electromagnetic radiation signal different from the signal obtained with an erythrocyte.

One particulate reagent (M) can be A and B positive erythrocyte to which a fluorescer is bound, either covalently or non-covalently e.g. through an antibody, which reagent will be referred to as E-$F_3$, where the fluorescer bound to the erythrocyte will be referred to as $F_3$. When reverse typing for determining αA or αB, antibodies to the erythrocyte will be for A or B determinants, respectively.

Other particles may be used to which the A and B antigens may be bound and which permit discrimination between an erythrocyte particle and the subject particle. Such particles include polymeric beads, such as polysaccharides an addition polymers, liposomes and erythrocyte ghosts, where the particles may or may not be labeled. The labels may be varied widely depending upon the nature of the particle and the distinguishing detectable signal.

One signal is light scatter where the scatter observed with the erythrocyte is different from the scatter observed with the M. Another signal is fluorescence, where the fluorescer bound to the particle has a different emission maximum or polarization from the other fluorescers present in the assay medium. Alternatively, the endogenous fluorescence or opacity of erythrocytes could provide the distinguishing parameter.

For light scatter one may use a number of different materials to label particles such as ghosts and liposomes. Colloidal metal or metal compounds, colloidal carbon, inks, etc. may be used. Alternatively, one can depend on the intrinsic light scattering difference between erythrocytes and erythrocyte ghosts, which scatter light less efficiently.

In addition to the erythrocyte reagents, labeled antibodies will also be used where the antibodies are specific for the particular phenotype.

In the subject assays, individual particles will be detected and the spectroscopic characteristics of these particles determined. By determining the presence or absence of the fluorescers on a particular particle, one can determine the phenotype of the host erythrocytes, as well as the presence of isoantibodies to the A and B antigens.

The following Table 2 is exemplary of the matrix of signals originating from individual particles which is diagnostic of the ABO type, as well as the presence of antibodies to the AB antigens, when employing $\alpha A\text{-}F_1$, $\alpha A\text{-}F_2$, and $M(A)B$.

TABLE 2*

|  | $F_1$ | $F_2$ | M |
| --- | --- | --- | --- |
| Blood Type | | | |
| A | + | − | − |
| B | − | + | − |
| AB | + | + | − |
| O | − | − | − |
| Isoantibodies | | | |
| $\alpha A$ | − | + | + |
| $\alpha B$ | + | − | + |
| $\alpha A \alpha B$ | − | − | + |
| − | + | + | + |

*$\alpha$ intends antibody
$F_1$ bound to $\alpha A$
$F_2$ bound to $\alpha B$
M bound to erythrocyte bearing A and B antigens-M(A)B
+ and − mean an elevated or reduced signal in relation to a defined signal level.

In analysing Table 2, one should consider that there will be at least two types of particles present in the sample: The marked particles having the A and B phenotypes and the host erythrocyte particle, whose phenotype is to be determined. The erythrocytes and marked particles can be readily distinquished. To illustrate the situation using a fluorescent marker $F_3$ on A and B particles, for A blood type, the host erythrocytes will bind to $\alpha A\text{-}F_1$. Therefore, when a host erythrocyte is observed, the emission and excitation from such erythrocyte will be at the wavelength band of $F_1$. The A and B phenotypic particle will be either $F_1+,F_2-,F_3+$ or $F_1+,F_2+,F_3+$ depending on whether or not $\alpha B$ antibodies are present. A similar analysis will follow for the other blood types.

The host erythrocytes will be distinguishable from the AB labeled particles, which if an erythrocyte, will be labeled with $F_3$. Therefore, those erythrocytes which do not fluoresce at the excitation and emission wavelength bands of $F_3$ will be the host erythrocytes and will be diagnostic for the presence of A and B antigens. When fluorescence is observed from a particle where there is emission in the wavelength band of $F_3$, one can determine whether there are antibodies to the A and/or B antigens by an elevated or reduced signal in the excitation and/or emission wavelength band of $F_1$ and $F_2$. Where antibodies to both A and B antigens are present, one would observe a reduced number of particles which fluoresce in the wavelength range of $F_3$ and also fluoresce in the wavelength ranges of $F_1$ and $F_2$.

As already indicated the A and B phenotype particle reagents will be distinguishable from the naturally occurring erythrocyte by a property which is detectable by a light signal. The light signal may be as a result of fluorescence, the particle being labeled with a fluorescer, or as a result of light scatter, the particle scattering light differently from an erythrocyte.

In accordance with the subject method, one is able to detect combinations of fluorescers which are present on single particles. This can be as a result of sequential or simultaneous measurement of the light emitted from a single particle. For simultaneous measurement, one would employ a detection means which permits differentiation of the different wavelengths resulting from the fluorescers and, as appropriate light scatter from each individual particle. For other than simultaneous measurements, a statistical anaylsis would be employed determining the incidence of the presence of a particular fluorescer associated with an erythrocyte or the marked particle. In this measurement a physical marker is not required. Rather, the "marked" particle must be present in substantially different ($>10$) concentration from the erythrocytes. This may be illustrated with a measurement for A and anti-A, where F-anti-A and unlabeled anti-A erythrocytes are employed. Initially, one would combine the blood sample and F-anti-A. One measures fluorescence where a positive result indicating the presence of A antigen is a predetermined population of particles having a fluorescent value above a threshold value. The unlabeled A erythrocytes are then added at a concentration at least equal to that of the host erythrocytes and a second fluorescent measurement is made. A negative result indicating the absence of anti-A will be a predetermined population of particles in excess of the population previously observed that have a fluorescent value above the threshold value.

Additionally, as previously described, different antibodies, each labeled with the same fluorescer, can be added sequentially to a suspension of host erythrocytes and a statistical measurement of the number of fluorescent particles made after each addition. The advantage, as indicated, is a simpler optical system.

Of particular interest is the use of the technique and apparatus described in copending application Ser. No. 397,285, filed July 12, 1982. The invention relies on the use of optical fibers which can address volumes, which are sufficiently small so that only single particles are interrogated as to their fluorescence. By employing splitters and appropriate filters, one can simultaneously measure fluorescent signals and light scatter at two or three different wavelength ranges or of different polarization. Thus, one can determine the concentration of particles which have a relatively large number of each of one or more of the different fluorescers. Since one is not concerned with the concentration of an individual fluorescer on the surface of the particle, but only whether a significant threshold number of such fluorescent molecules are present, the system need only discriminate between the different wavelength ranges and not as to the amount of fluorescence coming from the particle.

A useful device is exemplified in copending application Ser. No. 397,285, which may be employed without modification for sequential measurements. For simultaneous measurements, the device may be modified in accordance with the following description. The device has a sample holding means in which is immersed one or more optical fibers, which are divided into one to three brancehs, each branch having separate filters and/or polarizers which allow for the transmission of a signal corresponding to the fluorescence emission or light scatter of one of the fluorescers. Excitation light may be introduced through one of the branches or independently through a second optical fiber which illuminates the sample at the optical fiber probe face. Where the light is transmitted through the probe, a further fiber branch will be employed for providing the light source.

Another less preferred way is to employ two sources that could be used to excite at different wavelengths. One could then employ branches for introducing excitation light and eliminate the branches for the emission light.

A variety of sources of excitation light may be employed, preferably lasers, more particularly He-Cd, He-Ne or Ar lasers. Broad band light sources must be very intense and filters must be employed to ensure the proper wavelength range to avoid enhancing background interference. The light source should be small and the light beam directed to the area directly in front of the optical fiber probe.

The emission light which is received by the probe and transmitted through the branches will be received by a detector. The detector is any device capable of receiving photons and converting them to a signal form which permits differentiation between signals of different intensities. A photomultiplier is a typical example.

The electrons emitted in one photo-pulse by a photomultiplier tube may be directed to a preamplifier discriminator which amplifies the signal, discriminates against noise originating in the photomultiplier tube and generates a well-formed voltage pulse which may be counted by a digital counter. The number of photo-pulses per counter gate time is proportional to the intensity of light averaged over the gate time. These photo-pulse count values are interfaced to a computer which is programmed to detect changes in the count values, signifying a sharp fluctuation of fluorescence corresponding to the passage of a particle of interest through the effective sample volume. This is one example of how the signal from the light detector may be digitally analyzed. Alternatively, one could derive an analog signal from the detector and detect sharp transitions with a high-pass filter, or, combinations of analog and digital techniques can be used.

The frequency of fluctuations in the signal exceeding a threshold value is calculated and related to known calibrators. One can then determine the percentage of particles observed which have the various combinations of fluorescence emission for example as described above in Tables 1 and 2. The computer can then be programmed to automatically report the blood type in accordance with the observed fluorescent combinations above a predetermined threshold value.

In performing the subject invention, one or a plurality, usually not more than three, fluorescers are required. The fluorescer which may be conjugated to the erythrocyte is the least critical of the fluorescers for the following reasons. First, the fluorescer ($F_3$) can be conjugated in relatively large amounts to the erythrocyte. Therefore, where such fluorescer has a relatively low fluorescence efficiency, a greater amount of the fluorescer may be employed. Secondly, one only needs a sufficient amount bound to the erythrocyte, which will allow for assurance of its presence in combination with the other fluorescers. Therefore, one may choose a wide variety of fluorescers, which are primarily limited by not interfering with detection of the other two fluorescers. Conveniently, $F_3$ may have emission characteristics, where the emission maximum is less than 700, preferably less than 600, and more preferably between 450 and 510 nm.

The other fluorescers should have noninterfering emission maxima, generally having maxima different by at least about 20 nm, preferably by at least about 25 nm and should have high fluorescence efficiencies, be capable of binding to proteins without being detrimentally affected by the binding, as well as being minimally affected by non-specific interference. The fluorescers should have emission maxima greater than 450, preferably greater than 475, and more preferably greater than 500, where desirably the emission maxima of one will be in the range of about 500-575 and the emission maxima of the other will be in the range of about 550-625 nm. Fluorescers of particular interest may be found in EPO Application Ser. Nos. 80106587.1 and 80105253.1. Other fluorescers of interest include Texas Red, phycobiliproteins, derivatives of rhodamine, e.g., X-RITC, etc. The manner of conjugation of the fluorescers to the erythrocytes or the antibodies is widely described in the literature and need not be exemplified here. See for example, U.S. Pat. Nos. 4,199,559 and 4,318,846.

As an illustration of the use of three dyes, the first dye could be fluorescein or succinyl fluorescein; the second dye, 2,7-dimethoxy-4,5-dichloro-3',6'-dichloro-4' or 5'-carboxyfluorescein; and the third dye, Texas red. These dyes could be excited at 442 nm (He-Cd laser). Emission measurements would be made at 510±5, 560±15 and 610±15 nm respectively.

Alternatively, one may use coupled dyes, where a first dye or sensitizer absorbs light at shorter wavelengths and is capable of transferring energy to a second dye which is capable of fluorescence. In this way, one can use combinations of dyes, where one dye has high efficiency of absorption and will excite another dye which absorbs at higher wavelengths and has a high fluorescence efficiency. Sensitizers which find use include compounds of the following structure.

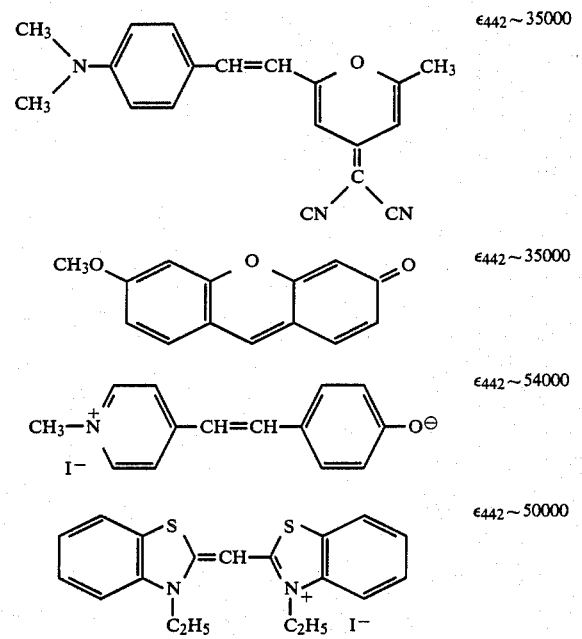

The sensitizers may be used by direct bonding to a fluorescer or by bonding to the molecule to which the fluorescer is bonded.

In preparing the subject conjugates, the following is an exemplary procedure.

To a cooled solution (0°-5°) of anti-A (7.5 mg) in 0.5 ml of 0.05M $PO_4^{3-}$ buffer pH 8.0 is slowly added a solution of N-hydroxy succinimide (NHS) ester of fluorescein (0.07 mg) in 25 μl DMF during 20 minutes. Stirring is continued overnight in the cold room. Next day the solution is centrifuged for 2 minutes and the yellow solution is purified over a Sephadex G-25 column using 0.05M $PO_4^{3-}$ buffer pH 8.0. The faster moving conjugate (1.5 ml) is easily separated. The conjugate has a $\lambda_{max}^{abs}$ 490 nm.

A sensitizer like the merocyanine compound can be attached through a $-CO_2H$ acid derivative, such as shown below:

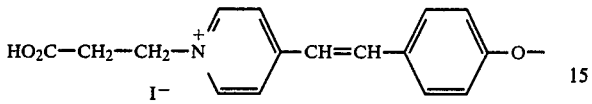

The above compound will be activated as the NHS ester and the NHS ester will be used to label antibodies as described above for labeling dyes.

In carrying out the blood typing, one may combine the reagent compositions with the blood sample sequentially or simultaneously. The blood sample may be used whole, but will normally be diluted by a factor of up to $10^3$, usually up to about $10^2$, in the assay medium. The sample and the reagents will normally be mixed in an aqueous buffered solution, generally at a pH in the range of about 5.0 to 9.5, which may include a variety of other materials, such as stabilizers, salts, inert powders, proteins, etc. The mixture will then be incubated for a sufficient time to allow for binding of the various antibodies to the determinant sites. Usually, at least thirty seconds will be employed and not more than about one hour, generally thirty minutes will suffice. One need not have reached equilibrium, since the primary concern is that there be sufficient binding to available antigenic determinants to allow for a sufficiently strong signal for a positive determination. The sample is then excited with appropriate light and the fluorescence emission determined, and light scatter or absorption determined, as appropriate. By analyzing for the combinations of fluorescence, in combination with the marker distinguishing the particle, one can determine the blood type and the presence of antibodies to the antigenic determinants for the ABO system. Or, if desired, other combinations of analytes.

In accordance with the subject invention, a rapid efficient method is provided for multiparameter analysis, such as in a single sample blood typing. The method allows for automation, so that determinations can be carried out quickly, efficiently, and with a minimum of technician handling. Results can be automatically computed and printed, so that the sample and results are easily and accurately related.

Although the foregoing invention has been described in some detail by way of illustration and example for purposes of clarity of understanding, it will be obvious that certain changes and modifications may be practiced within the scope of the appended claims.

What is claimed is:

1. A method for determining a plurality of blood typing parameters, said parameters being epitopic sites and binding sites of specific binding members ($SBM_1$, $SBM_2$, ... $SBM_m$), said binding members being ligands and reciprocal receptors respectively, wherein at least one parameter containing specific binding member or its reciprocal specific binding member is bound to a particle (SBM-P or RSBM-P), said method involving at least one fluorescent label bound to a specific bindng member (SBM-F) and at least one particle (P), different fluorescent labels and different particles being distinguishable by spectroscopic characteristics, which are emission, absorption and light scattering;

said method comprising:
combining in a liquid medium,
(a) a blood sample having at least two blood typing parameters to be measured;
(b) for parameter containing specific bindng members bound to a particle ($SBM_1$-$P_1$, $SBM_2$-$P_2$, ... $SBM_m$-$P_m$), fluorescent labeled specific binding member reciprocal to said specific binding member bound to said particle ($RSBM_1$-$F_1$, $RSBM_2$-$F_2$, ... $RSBM_m$-$F_m$);
(c) for parameter containing specific binding members not bound to a particle ($SBM_1$, $SBM_2$, ... $SBM_m$), (1) a particle bound to a specific binding member reciprocal to said parameter containing specific binding member ($RSBM_1$-$P_1$, $RSBM_2$-$P_2$, ... $RSBM_m$-$P_m$) and (2) a fluorescent labeled specific binding member analogous to said parameter containing specific binding member ($SBM_1$-$F_1$, $SBM_1$-$F_1$ ... $SBM_m$-$F_m$);
wherein the number of different particles ($P_m$) and fluorescent labels ($F_m$) are chosen to give signals (n) that distinguish each parameter in said sample and wherein sequential additions and sequential measurements may be made or simultaneous additions and simultaneous measurements may be made, and wherein n signals can distinguish $2^{n-1}$ parameters and wherein reciprocal binding members bind with each other;
irradiating at least a portion of said medium with light, wherein said medium is continuous and said particles are suspended in said continuous medium, and determining populations of particles having electromagnetic signals differing from threshold values; and
relating said populations to the presence of said parameters in said sample.

2. A method according to claim 1, wherein said sample is whole blood.

3. A method according to claim 2, wherein said parameters are determinant sites on an erythrocyte.

4. A method according to claim 1, having two particles which differ by distinguishable electromagnetic signals produced upon irradiation with light.

5. A method according to claim 4, where one of said particles is labeled with a fluorescer and the other of said particles is not labeled with a fluorescer.

6. A method according to claim 5, wherein two particles are present, one particle is an erythrocyte from said sample and the other particle is a fluorescer labeled erythrocyte.

7. A method according to claim 1, wherein individual particles are monitored for their fluorescence within a predetermined wavelength range by monitoring a sample volume sufficiently small to have a high probability of having no or one particle.

8. A method for determining a plurality of blood typing parameters, said parameters being epitopic sites and binding sites of specific binding members ($SBM_1$, $SBM_2$, ... $SBM_m$), said binding members being ligands and reciprocal receptors, respectively, wherein at least one parameter containing specific binding member is bound to a particle (SBM-P), said method involving one fluorescent label bound to at least one member (SBM-F) and at least one particle (P);

said method comprising:

combining in a liquid medium, (a) a blood sample having at least two blood typing parameters to be measured;

(b) in sequential additions as to each parameter:

(i) where a parameter containing specific binding member is bound to a particle ($SBM_1$-$P_1$, $SBM_2$-$P_2$, ... $SBM_m$-$P_m$), fluorescer labled specific binding member reciprocal to said parameter contaning specific binding member ($RSBM_1$-$F_1$, $RSBM_2$-$F_2$, ... $RSBM_m$-$F_m$);

(ii) where a parameter containing specific binding member is unbound ($SBM_1$, $SBM_2$, ... $SBM_m$), (1) a particle having the reciprocal specific binding member ($RSBM_1$-$P_1$, $RSBM_2$-$P_2$, ... $RSBM_m$-$P_m$); and (2) a fluorescer labeled specific binding member analogous to said parameter containing specific binding member ($SBM_1$-$F_1$, $SBM_2$-$F_2$, ... $SBM_m$-$F_m$);

wherein the number of different particles and fluorescent labels are chosen to give signals (n) that distinguish each parameter in said sample and wherein sequential additions and sequential measurements may be made or simultaneous additions and simultaneous measurements may be made, and wherein n signals can distinguish $2^{n-1}$ parameters and wherein reciprocal binding members bind with each other;

with the proviso that, when only the fluorescer labeled specific binding member (SBM-F) is added in the second addition, there will be at least about a 2-fold increase in binding events relative to the binding events that have already occurred; and when a particle (P) is added in the second addition the number of particles in the medium will be at least about doubled;

irradiating at least a portion of said medium with light, wherein said medium is continuous and said particles are suspended in said continuous medium;

determining the population of particles differing from a threshold value as to an electromagnetic signal after the first addition and the population of particles differing from a threshold value as to an electromagnetic signal after the second addition and so on for each parameter in said sample; and relating said populations to the presence of said parameters in said sample.

9. A method for determining a plurality of parameters, said parameters being epitopic sites and binding sites of specific binding members ($SBM_1$, $SBM_2$, ... $SBM_m$), said binding members being ligands and reciprocal receptors respectively, wherein at least one parameter containing specific binding member or its reciprocal specific binding member is bound to a particle which is an erythrocyte (SBM-P or RSBM-P), said method involving at least one fluorescent label bound to a specific binding member (SBM-F) and at least one particle (P), different fluorescent labels and different particles being distinguishable by spectroscopic characteristics, which are emission, absorption and light scattering;

said method comprising:

combining in a liquid medium, (a) a sample having at least two parameters to be measured;

(b) for parameter containing specific binding members bound to a particle ($SBM_1$-$P_1$, $SBM_2$-$P_2$, ... $SBM_m$-$P_m$), fluorescent labeled specific binding member reciprocal to said specific bindng member bound to said particle ($RSBM_1$-$F_1$, $RSBM_2$-$F_2$, ... $RSBM_m$-$F_m$);

(c) for parameter containing specific binding members not bound to a particle ($SBM_1$, $SBM_2$, ... $SBM_m$), (1) a particle bound to a specific binding member reciprocal to said parameter containing specific binding member ($RSBM_1$-$P_1$, $RSBM_2$-$P_2$, ... $RSBM_m$-$P_m$ and (2) a fluorescent labeled specific binding member analogous to said parameter containing specific binding member ($SBM_1$-$F_1$, $SBM_2$-$F_2$ ... $SBM_m$-$F_m$;

wherein the number of different particles ($P_m$) and fluorescent labels ($F_m$) are chosen to give signals (n) that distinguish each parameter in said sample and wherein sequential additions and sequential measurements may be made or, simultaneous additions and simultaneous measurements may be made, and wherein n signals can distinguish $2^{n-1}$ parameters and wherein reciprocal binding members bind with each other and wherein individual particles are monitored in a non-flow system for their fluorescence within a predetermined wavelength range by monitoring a sample volume sufficiently small to have a high probability of having no or one particle;

irradiating at least a portion of said medium with light, wherein said medium is continuous and said particles are suspended in said continuous medium, and determining populations of particles having electromagnetic signals differing from threshold values; and relating said populations to the presence of said parameters in said sample.

10. A method according to claim 9, wherein said sample is whole blood.

11. A method according to claim 9, having two particles which differ by distinguishable electromagnetic signals produced upon irradiation with light.

12. A method according to claim 11, where one of said particles is labeled with a fluorescer and the other of said particles is not labeled with a fluorescer.

13. A method according to claim 12, wherein two particles are present, one particle is an erythrocyte from said sample and the other particle is a fluorescer labeled erythrocyte.

14. A method for determining a plurality of parameters, said parameters being epitopic sites and binding sites of specific binding members ($SBM_1$, $SBM_2$, ... $SBM_m$), said binding members being ligands and reciprocal receptors, respectively, wherein at least one parameter containing specific binding member is bound to a particle (SBM-P), said method involving one fluorescent label bound to at least one member (SBM-F) and at least one particle (P);

said method comprising:

combining in a liquid medium, (a) a sample having at least two parameters to be measured;

(b) in sequential additions as to each parameter:

(i) where a parameter containing specific binding member is bound to a particle ($SBM_1$-$P_1$, $SBM_2$-$P_2$, ... $SBM_m$-$P_m$), fluorescer labeled specific binding member reciprocal to said parameter containing specific binding member ($RSBM_1$-$F_1$, $RSBM_2$-$F_2$, ... $RSBM_m$-$F_m$);

(ii) where a parameeter containing specific binding member is unbound ($SBM_1$, $SBM_2$, ... $SBM_m$),
(1) a particle having the reciprocal specific binding member ($RSBM_1$-$P_1$, $RSBM_2$-$P_2$, ... $RSBM_m$-$P_m$); and (2) a fluorescer labeled specifc binding member analogous to said parameter containing specific binding member ($SBM_1$-$F_1$, $SBM_2$-$F_2$, ... $SBM_m$-$F_m$);

wherein the number of different particles and fluorescent labels are chosen to give signals (n) that distinguish each parameter in said sample and wherein sequential additions and sequential measurements may be made or simultaneous additions and simultaneous measurements may be made, and wherein n signals can distinguish $2^{n-1}$ parameters and wherein reciprocal binding members bind with each other and wherein individual particles are monitored in a non-flow system for their fluorescence within a predetermined wavelength range by monitoring a sample volume sufficiently small to have a high probability of having no or one particle;

with the proviso that, when only the fluorescer labeled specific binding member (SBM-F) is added in the second addition, there will be at least about a 2-fold increase in binding events relative to the binding events that have already occurred; and when a particle (P) is added in the second addition the number of particles in the medium will be at least about doubled;

irradiating at least a portion of said medium with light, wherein said medium is continuous and said particles are suspended in said continuous medium;

determining the population of particles differing from a threshold value as to an electromagnetic signal after the first addition and the population of particles differing from a threshold value as to an electromagnetic signal after the second addition and so on for each parameter in said sample; and relating said populations to the presence of said parameters in said sample.

* * * * *